US006306374B1

(12) United States Patent
Ramin et al.

(10) Patent No.: US 6,306,374 B1
(45) Date of Patent: Oct. 23, 2001

(54) NAIL CARE COMPOSITION COMPRISING A WATER-DISPERSIBLE POLYCONDENSATE AND A WATER-SOLUBLE COPOLYMER

(75) Inventors: Roland Ramin, Itteville; Jean Mondet, Aulnay-sous-Bois, both of (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 08/501,822

(22) Filed: Jul. 13, 1995

(30) Foreign Application Priority Data

Jul. 13, 1994 (FR) .................................. 94 08731

(51) Int. Cl.$^7$ ................ A61K 6/00; A61K 7/00; A61K 7/04
(52) U.S. Cl. .............................. 424/61; 424/401
(58) Field of Search .................... 424/61, 401, 10.11

(56) References Cited

U.S. PATENT DOCUMENTS

| 3,928,113 | * | 12/1975 | Rosenberg | 156/344 |
| 4,666,709 | * | 5/1987 | Jankewitz | 424/61 |
| 5,266,322 | | 11/1993 | Myers et al. | |

FOREIGN PATENT DOCUMENTS 2 148 714    6/1985   (GB) .

OTHER PUBLICATIONS

Discolsed Anonymously, "Fast Drying Aqueous Nail Polish", *Research Disclosure*, 1991, p. 3995, vol. 326.

* cited by examiner

Primary Examiner—Thurman K. Page
Assistant Examiner—S. Howard
(74) Attorney, Agent, or Firm—Oblon, Spivak, McClelland, Maier & Neustadt, P.C.

(57) ABSTRACT

A composition containing:
- a) 5 to 50% by weight relative to the total weight of the composition of a water-dispersible polycondensate containing sulphonate functional groups,
- b) 0.5 to 20% by weight relative to the total weight of the composition of a water-soluble copolymer containing carboxylic acid functional groups neutralized in a proportion of at least 80% with a nonvolatile basic agent, the weight average molecular weight of said copolymer being between 1,000 and 700,000, and
- c) 0.01 to 0.5% by weight relative to the total weight of the composition of a nail care active principle, in an aqueous or aqueous-alcoholic medium,
  provides a nail coating composition which is readily applicable to the nail, dries rapidly and leaves a protective film on the nail.

23 Claims, No Drawings

NAIL CARE COMPOSITION COMPRISING A WATER-DISPERSIBLE POLYCONDENSATE AND A WATER-SOLUBLE COPOLYMER

BACKGROUND OF THE INVENTION

1. Field of the Invention

The present invention relates to a nail care composition containing, in an aqueous or weakly aqueous-alcoholic medium, the combination of a water-dispersible polycondensate containing sulphonate functional groups and a water-soluble copolymer containing at least units having a neutralized carboxylic acid functional group, and at least one nail care active principle.

2. Discussion of the Background

The nails can present various problems. They can, in particular, be damaged by organic solvent-based nail varnishes or, alternatively, by compositions which dissolve these varnishes.

With a view to protecting the nails from the harm caused, in particular, by the presence of organic solvents, various base compositions have been proposed, to be applied prior to the application of the varnish, these compositions playing essentially the part of a physical barrier in order to avoid contact of the varnish with the nail.

Thus, in Application JP 92-103511, nail varnish, base or pre-coating compositions have been described, based on an aqueous emulsion of a polymer of cationic, nonionic or amphoteric nature, but preferably cationic, prepared by polymerization of hydrophobic monomers and monomers containing tertiary amine groups, optionally neutralized with an inorganic or organic acid. These base compositions display some degree of resistance to water, and are removed only at the same time as the nail varnish by means of a dissolving agent containing organic solvents.

Moreover, the nails may also be damaged by frequent contact with detergents or, alternatively, by the use of aqueous nail varnishes of the peelable type, the removal of which brings about a desquamation of the keratin of the nail.

It is desirable to have compositions not displaying any toxicity for the nails, the removal of which would not be detrimental to the nails and which, in addition, would enable the active principle or principles intended for treating the various problems mentioned above to be efficiently applied on the surface of the nail.

In order to be satisfactory, these compositions must, furthermore, be readily applicable to the nail, dry fairly rapidly and leave after drying a film which must, on the one hand cover the whole of the surface of the nail, and on the other hand display good adhesion.

SUMMARY OF THE INVENTION

It has now been found, surprisingly and unexpectedly, that nail care compositions displaying the above mentioned properties are obtained by combining, in an aqueous or aqueous-alcoholic vehicle, a water-dispersible polycondensate containing sulphonate functional groups, a water-soluble copolymer containing neutralized carboxylic acid functional groups and at least one nail care active principle.

DETAILED DESCRIPTION OF THE PREFERRED EMBODIMENTS

The subject of the present invention is a nail care composition containing, in an aqueous or aqueous-alcoholic medium:

a) from 5 to 50% by weight relative to the total weight of the composition of a water-dispersible polycondensate containing sulphonate functional groups, b) from 0.5 to 20% by weight relative to the total weight of the composition of a water-soluble copolymer containing carboxylic acid functional groups neutralized in a proportion of at least 80% with a nonvolatile basic agent, the weight average molecular weight of the copolymer being between 1,000 and 700,000, and c) from 0.01 to 0.5% by weight relative to the total weight of the composition of a nail care active principle.

Preferably, the composition according to the invention contains from 10 to 25% by weight relative to the total weight of the composition of the water-dispersible polycondensate as defined above, and preferably from 2 to 10% by weight relative to the total weight of the composition of the water-soluble copolymer as defined above.

According to an embodiment of the compositions according to the invention, the ratio by weight of the water-soluble copolymer to the water-dispersible polycondensate is between 0.05 and 0.4, and preferably between 0.1 and 0.3.

The water-dispersible polycondensates containing sulphonate functional groups used according to the invention generally have a glass transition temperature of between 10° C. and 100° C., and preferably between 25° C. and 60° C.

Water-dispersible polycondensates containing sulphonate functional groups are preferably understood, according to the invention, to mean copolyesters or copolyesteramides. The copolyesters are obtained by polycondensation of at least one dicarboxylic acid or one of its esters, at least one diol and at least one bifunctional sulphoaryldicarboxylic compound substituted on the aromatic ring system with an —$SO_3M$ group in which M represents a hydrogen atom or a metal ion such as $Na^+$, $Li^+$ or $K^+$.

The copolyesteramides are obtained in the same manner as the copolyesters, but the polycondensation also involves a diamine and/or an amino alcohol.

The water-dispersible polycondensates as defined above are known, and have been described, in particular, in U.S. Pat. No. 3,779,993, U.S. Pat. No. 4,300,580 and EP 0,540,374 which are incorporated herein by reference.

They generally have a weight average molecular weight of between about 1,000 and 60,000, and preferably of about 14,000.

Preferably, the water-dispersible polycondensates containing sulphonate functional groups used according to the invention display the common feature of comprising at least some units derived from isophthalic acid, from a sulphoaryldicarboxylic acid salt and from diethylene glycol.

According to a particular embodiment of the composition according to the invention, the water-dispersible polycondensates containing sulphonate functional groups used are copolyesters consisting of units derived from isophthalic acid, from sulphoisophthalic acid sodium salt, from diethylene glycol and from 1,4-cyclohexanedimethanol, these preferably being present in proportions of 89:11:78:22 or 82:18:54:46. These polycondensates are marketed, respectively, under the trade names "AQ 38®" and "AQ 55®" by the company Eastman Kodak.

According to another embodiment of the compositions according to the invention, the water-dispersible polycondensates used can contain, in addition, units derived from ethylene glycol, from tri- and tetraethylene glycol and from terephthalate.

The water-soluble copolymers containing carboxylic acid functional groups used according to the invention are synthetic polymers, and are preferably selected from the group consisting of:

a) polyoxyethylenated vinyl acetate/crotonic acid copolymers,
b) N-octylacrylamide/methyl methacrylate/hydroxylpropyl methacrylate/acrylic acid/tert-butylaminoethyl methacrylate copolymers,
c) methyl vinyl ether/maleic anhydride alternating copolymers monoesterified with butanol,
d) acrylic acid/ethyl acrylate/N-tert-butylacrylamide terpolymers, and
e) the copolymers corresponding to the following formula (I):

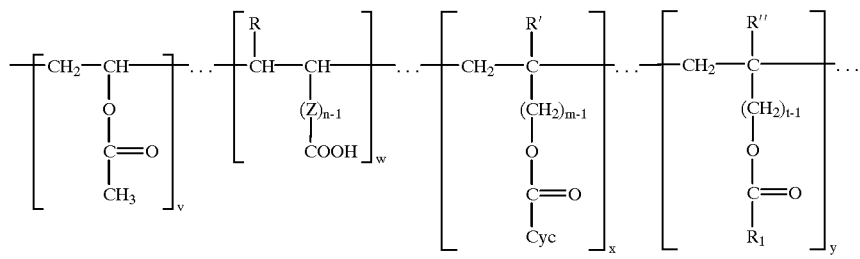

in which:
R, R' and R", which may be identical or different, are a hydrogen atom or a methyl group,
m, n and t are 1 or 2,
$R_1$ is a saturated or unsaturated, linear or branched alkyl group having from 2 to 21 carbon atoms,
Z is a bivalent group taken from the group consisting of $-CH_2-$, $-CH_2-O-CH_2-$ and $-CH_2O-(CH_2)_2-$,
and Cyc is a group selected from the group consisting of:
(i) a group of formula:

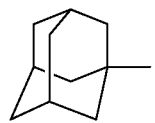

(ii) a group of formula:

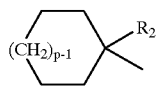

in which:
$R_2$ is a hydrogen atom or a methyl group, and p is 1 or 2,
(iii) a group of formula:

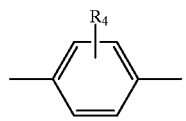

in which:
$R_3$ is a hydrogen atom or a methyl, ethyl, tert-butyl, ethoxy, butoxy or dodecyloxy group and $R_4$ is a hydrogen atom, an alkyl group having 1 to 4 carbon atoms or an alkoxy group having 1 to 4 carbon atoms, and (iv) a group of formula:

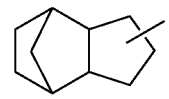

v is from 10 to 97% and preferably from 36 to 90% by weight,
w is from 3 to 20% and preferably from 6 to 12% by weight,
x is from 0 to 60% and preferably from 6 to 40% by weight, and
y is from 0 to 40% and preferably from 4 to 30% by weight,
v+w+x+y being equal to 100%.

Among polyoxyethylenated vinyl acetate/crotonic acid copolymers, "ARISTOFLEX A®" of acid value 56 of the company Hoechst may be mentioned in particular.

As an N-octylacrylamide/methyl methacrylate/hydroxypropyl methacrylate/acrylic acid/tert-butylaminoethyl methacrylate copolymer, "AMPHOMER®" of acid value 137 of the company National Starch may be mentioned.

Among methyl vinyl ether/maleic anhydride alternating copolymers monoesterified with butanol, "GANTREZ ES 425®" of acid value 260 of the company GAF may be mentioned.

As acrylic acid/ethyl acrylate/N-tert-butylacrylamide terpolymers, special mention may be made of "ULTRA-HOLD 8®" of acid value 62 of the company BASF.

As water-soluble copolymers corresponding to the formula (I) defined above, the following may be mentioned in particular:
vinyl acetate/crotonic acid (90:10) copolymer, such as the one marketed under the name "LUVISET CA 66®" of acid value 74 by the company BASF, and
vinyl acetate/crotonic acid/vinyl neodecanoate terpolymers, such as the one marketed under the name "RESYN 28-2930®" of acid value 65 by the company National Starch.

As water-soluble copolymers containing carboxylic acid functions corresponding to the formula (I) defined above, the ones described in FR 78/30596 (2,439,798) may also be mentioned, and especially the following copolymers:
Vinyl acetate/crotonic acid/vinyl 4-tertbutylbenzoate/vinyl neodecanoate (57:10:25:8) and (70:10:10:10),
Vinyl acetate/crotonic acid/vinyl 4-tertbutylbenzoate (65:10:25),
Vinyl acetate/crotonic acid/vinyl benzoate/vinyl neodecanoate (70:10:10:10), and
Vinyl acetate/crotonic acid/vinyl 4-tert-butyl-benzoate/allyl stearate (70:10:10:10).

Preferably, the water-soluble copolymer used in the compositions according to the invention is selected from the copolymers of formula (I), and more especially from vinyl acetate/crotonic acid (90:10) and vinyl acetate/crotonic acid/vinyl 4-tert-butylbenzoate (65:10:25) copolymers.

These copolymers are not used as such in the compositions according to the invention, but their carboxylic acid functions must be neutralized beforehand.

Preferably, they are neutralized to a degree of 100%, using a base selected, for example, from an inorganic base such as sodium hydroxide or potassium hydroxide or an organic base chosen from the group consisting of 2-amino-2-methyl-1-propanol (AMP), triethanolamine, triisopropanolamine (TIPA), monoethanolamine, diethanolamine, tris(2-hydroxy-1-propyl) amine, 2-amino-2-methyl-1,3-propanediol (AMPD) and 2-amino-2-hydroxymethyl-1,3-propanediol.

Among the nail active principles which may be incorporated in the nail care compositions according to the invention, the following substances are well known nail active principles:

a) vitamins and their derivatives such as:
  vitamin A derivatives such as retinol palmitate,
  vitamin $B_5$ and its derivatives such as panthenol, panthenol palmitate, panthenol triacetate, calcium pantothenate and pantetheine,
  vitamin $D_3$ or cholecalciferol,
  vitamin E derivatives such as tocopherol acetate, tocopherol linoleate and tocopherol nicotinate,
  vitamin F or essential fatty acids containing a high percentage of linoleic acid, and
  vitamin H or biotin, b) proteins, their derivatives and hydrolysates, such as:
  keratin and keratin hydrolysates,
  silk proteins,
  collagen and its derivatives,
  soya protein hydrolysates, and
  proteins originating from wheat hydrolysates, c) trace elements such as:
  zinc gluconate, copper gluconate, iron gluconate, magnesium gluconate or manganese gluconate, and (d) various active substances such as: chitosan and its derivatives such as chitosan glutamate and carboxymethylchitin, melanin, hyaluronic acid, magnesium carbonate, glycerol, urea, formaldehyde and phospholipids such as soya bean lecithin.

In the compositions according to the invention, the proportion of water is generally between 27.50 and 94.49% by weight relative to the total weight of the composition.

When the vehicle is an aqueous-alcoholic solution, the proportion of alcohol is relatively low and is preferably between 0.1 and 10% relative to the total weight of composition, and more preferably between 0.1 and 3%. The alcohols which can be used are preferably alcohols having from 2 to 5 carbon atoms, and especially ethanol, isopropanol or n-butanol, polyols having from 2 to 8 carbon atoms and from 2 to 4 hydroxyl groups or glycols such as dipropylene glycol.

Compositions according to the invention can contain, in addition, a plasticizing agent in a proportion not exceeding 10% by weight relative to the total weight of the composition.

Among plasticizing agents which may be used, the following may be mentioned:

CARBITOLS® of the company Union Carbide, namely CARBITOL or diethylene glycol ethyl ether, METHYL CARBITOL or diethylene glycol methyl ether, BUTYL CARBITOL or diethylene glycol butyl ether or alternatively HEXYL CARBITOL or diethylene glycol hexyl ether, CELLOSOLVES® of the company Union Carbide, namely CELLOSOLVE or ethylene glycol ethyl ether, BUTYL CELLOSOLVE or ethylene glycol butyl ether, or HEXYL CELLOSOLVE or ethylene glycol hexyl ether, propylene glycol derivatives, and especially propylene glycol phenyl ether, propylene glycol diacetate, dipropylene glycol butyl ether, tripropylene glycol butyl ether, as well as DOWANOLS® of the company Dow Chemical, namely DOWANOL PM or propylene glycol methyl ether, DOWANOL DPM or dipropylene glycol methyl ether, and DOWANOL TPM or tripropylene glycol methyl ether.

The following may also be mentioned:

diethylene glycol methyl ether or DOWANOL DM® of the company Dow Chemical, oxyethylenated castor oil containing 40 mol of ethylene oxide, such as the one sold by the company Rhone Poulenc under the name "MULGOFEN EL-719®", benzyl alcohol, triethyl citrate, sold by the company Pfizer under the name "CITROFLEX-2®", 1,3-butylene glycol, diethyl, dibutyl and diisopropyl phthalates and adipates, diethyl and dibutyl tartrates, diethyl, dibutyl and di(2-ethylhexyl) phosphates, and glycerol esters such as glyceryl diacetate (diacetin) and glyceryl triacetate (triacetin).

The compositions according to the invention can contain, in addition, at least one cosmetic additive in a proportion of between 0.01 and 2% by weight relative to the total weight of composition.

Among cosmetic additives which may be incorporated in the composition according to the invention, water-soluble thickeners, ultraviolet screening agents, perfumes, colorants and pigments may be mentioned in particular.

As water-soluble thickeners, special mention may be made of cellulose derivatives, water-soluble synthetic polymers and water-soluble associative polyurethanes.

The compositions according to the invention can take the form, in particular, of lotions or gels, which may be applied by means of a brush.

The film obtained after application and drying of the composition adheres well to the nail but is nevertheless readily removable with water.

Should the user then wish to make up the nail, she can either remove the composition before application of the colored nail varnish, or apply it directly to the film left by the composition according to the invention.

Several non-limiting examples of compositions according to the invention will now be given by way of illustration.

EXAMPLES

Example 1

To a dispersion obtained by mixing, with vigorous stirring, 75.50 g of water at a temperature of 80° C. and 16 g of the isophthalic acid/sulphoisophthalic acid sodium salt/diethylene glycol/1,4-cyclohexanedimethanol (89:11:78:22) polycondensate in solid form, marketed under the name "AQ 38®" by the company Eastman Kodak, and after cooling to room temperature, the following compounds were added:

| | |
|---|---|
| Vinyl acetate/crotonic acid/vinyl 4-tert-butyl-benzoate (65:10:25) terpolymer 100% neutralized by means of 2-amino-2-methyl-1-propanol | 5.0 g |
| Glycerol | 3.0 g |
| D-Panthenol | 0.5 g |

The composition thereby obtained was applied to the nails by means of a brush. After drying in 5 to 10 minutes, a glossy and translucent film coating the surface of the nails was obtained. This film was readily removed with water, whether after a few minutes or after several hours.

A daily application of this composition for several weeks to initially brittle nails considerably improved their general state, and especially their strength.

Example 2

According to the same procedure as described in Example 1, a nail treatment composition was prepared by mixing the following compounds:

| | |
|---|---|
| Isophthalic acid/sulphoisophthalic acid sodium salt/diethylene glycol/1,4-cyclohexanedimethanol (89:11:78:22) polycondensate | 30 g |
| Vinyl acetate/crotonic acid/vinyl 4-tert-butyl-benzoate (65:10:25) terpolymer 100% neutralized by means of 2-amino-2-methyl-1-propanol | 15 g |
| Formaldehyde | 0.20 g |
| Water | 48.8 g |

To the mixture thereby obtained, 6 g of hydroxypropylcellulose gel, prepared according to known methods from 5 g of hydroxypropylcellulose and 95 g of water, were added.

The composition thereby obtained was applied readily to the nails. After drying for 5 to 10 minutes, a glossy and translucent film covering the whole of the nail, and which may be readily removed with water, was obtained.

A daily application of this composition for several weeks considerably improved the hardness of the nails.

Example 3

According to the same procedure as described in Example 1, a nail treatment composition was prepared by mixing the following compounds:

| | |
|---|---|
| Isophthalic acid/sulphoisophthalic acid sodium salt/diethylene glycol/1,4-cyclohexanedimethanol (82:18:54:46) polycondensate | 13.5 g |
| vinyl acetate/crotonic acid (90:10) copolymer 100% neutralized by means of 2-amino-2-methyl-1-propanol | 4.5 g |
| Glycerol | 3 g |
| Propylene glycol | 5 g |
| D-Panthenol | 0.5 g |
| Water | 73.5 g |

On application of this composition to the nails, the same properties were observed as in Examples 1 and 2.

Obviously numerous modifications and variations of the present invention are possible in light of the above teachings. It is, therefore, to be understood that within the scope of the appended claims, the invention may be practiced otherwise than as specifically described therein.

What is claimed as new and desired to be secured by Letters Patent of the United States is:

1. A nail care composition, comprising:
   a) 5 to 50% by weight relative to the total weight of the composition of a water-dispersible polycondensate containing sulphonate functional groups,
   b) 0.5 to 20% by weight relative to the total weight of the composition of a water-soluble copolymer containing carboxylic acid functional groups neutralized in a proportion of at least 80% with a nonvolatile base, the weight average molecular weight of the said copolymer being between 1,000 and 700,000, and
   c) 0.01 to 0.5% by weight relative to the total weight of the composition of a nail care active component,
   in an aqueous or aqueous-alcoholic medium.

2. The composition of claim 1, comprising 10 to 25% by weight relative to the total weight of the composition of said water-dispersible polycondensate.

3. The composition of claim 1, comprising 2 to 10% by weight relative to the total weight of the composition of said water-soluble copolymer.

4. The composition of claim 1, wherein the ratio by weight of the said water-soluble copolymer to said water-dispersible polycondensate is between 0.05 and 0.4.

5. The composition of claim 1, wherein the ratio by weight of said water-soluble copolymer to said water-dispersible polycondensate is between 0.1 and 0.3.

6. The composition of claim 1, wherein said polycondensate has a glass transition temperature of between 10° C. and 100° C.

7. The composition of claim 1, wherein said polycondensate has a glass transition temperature of between 25° C. and 60° C.

8. The composition of claim 1, wherein said water-dispersible polycondensate containing sulphonate functional groups is a copolyester or a copolyesteramide.

9. The composition of claim 8, wherein said copolyester is a polycondensate of at least one dicarboxylic acid or an ester thereof, at least one diol and at least one bifunctional sulphoaryldicarboxylic acid substituted on an aromatic ring thereof with an —$SO_3M$ group, in which M is a hydrogen atom or a metal ion selected from the group consisting of $Na^+$, $Li^+$ and $K^+$.

10. The composition of claim 8, wherein said copolyesteramide is a polycondensate of at least one dicarboxylic acid or ester thereof, at least one diol, at least one bifunctional sulphoaryldicarboxylic acid substituted on an aromatic ring thereof with an —$SO_3M$ group, in which M is a hydrogen atom or a metal ion selected from the group consisting of $Na^+$, $Li^+$ and $K^+$, and at least one diamine, amino alcohol or mixture thereof.

11. The composition of claim 1, wherein said water-soluble copolymer is selected from the group consisting of:
   a) polyoxyethylenated vinyl acetate/crotonic acid copolymers,
   b) N-octylacrylamide/methyl methacrylate/hydroxylpropyl methacrylate/acrylic acid/tert-butylaminoethyl methacrylate copolymers,
   c) methyl vinyl ether/maleic anhydride alternating copolymers monoesterified with butanol,
   d) acrylic acid/ethyl acrylate/N-tert-butylacrylamide terpolymers, and
   e) copolymers having the formula (I):

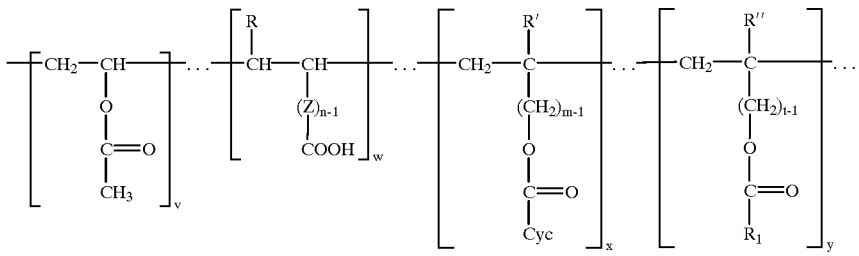

wherein R, R' and R", which may be identical or different, are a hydrogen atom or a methyl group,
m, n and t are 1 or 2,
$R_1$ is a saturated or unsaturated, linear or branched alkyl group having from 2 to 21 carbon atoms,
Z is a bivalent group selected from the group consisting of —$CH_2$—, —$CH_2$—O—$CH_2$— and —$CH_2O$—($CH_2$)$_2$—,
and Cyc is a group selected from the group consisting of:
(i) a group of formula:

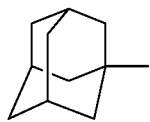

(ii) a group of formula:

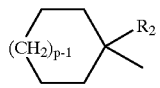

wherein $R_2$ is a hydrogen atom or a methyl group, and p is 1 or 2,
(iii) a group of formula:

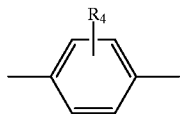

wherein $R_3$ is a hydrogen atom or a methyl, ethyl, tert-butyl, ethoxy, butoxy or dodecyloxy group and
$R_4$ is a hydrogen atom, an alkyl group having 1 to 4 carbon atoms or an alkoxy group having 1 to 4 carbon atoms, and
(iv) a group of formula:

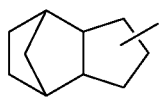

v is from 10 to 97% by weight,
w is from 3 to 20% by weight,
x is from 0 to 60% by weight, and
y is from 0 to 40% by weight,
v+w+x+y being equal to 100%.

12. The cosmetic composition of claim 11, wherein said water-soluble copolymer of formula (I) is selected from the group consisting of:
Vinyl acetate/crotonic acid (90:10),
Vinyl acetate/crotonic acid/vinyl 4-tert-butylbenzoate (65:10:25),
Vinyl acetate/crotonic acid/vinyl neodecanoate,
Vinyl acetate/crotonic acid/vinyl 4-tertbutylbenzoate/vinyl neodecanoate (57:10:25:8) and (70:10:10:10),
Vinyl acetate/crotonic acid/vinyl benzoate/vinyl neodecanoate (70:10:10:10), and
Vinyl acetate/crotonic acid/vinyl 4-tertbutylbenzoate/allyl stearate (70:10:10:10).

13. The composition of claim 11, wherein said water-soluble copolymer is selected from the group consisting of vinyl acetate/crotonic acid (90:10) and vinyl acetate/crotonic acid/vinyl 4-tert-butylbenzoate (65:10:25) copolymers.

14. The composition of claim 1, wherein said carboxylic acid functional groups of the said water-soluble copolymer are 100% neutralized.

15. The composition of claim 1, wherein said carboxylic acid functional groups of said water-soluble copolymer are neutralized with a non-volatile base selected from the group consisting of sodium hydroxide, potassium hydroxide, 2-amino-2- methylpropanol, triethanolamine, triisopropanolamine, monoethanolamine, diethanolamine, tris(2-hydroxy-1-propyl) amine, 2-amino-2-methyl-1,3-propanediol and 2-amino-2-hydroxymethyl-1,3-propanediol.

16. The composition of claim 1, wherein said nail care active component is selected from the group consisting of vitamins, proteins, trace elements, chitosan, melanin, hyaluronic acid, magnesium carbonate, glycerol, urea, formaldehyde, phospholipids and mixtures thereof.

17. The composition of claim 1, further comprising a plasticizing agent in a proportion up to 10% by weight relative to the total weight of the composition.

18. The composition of claim 17, wherein said plasticizing agent is selected from the group consisting of diethylene glycol ethyl ether, diethylene glycol methyl ether, diethylene glycol butyl ether, diethylene glycol hexyl ether, ethylene glycol ethyl ether, ethylene glycol butyl ether, ethylene glycol hexyl ether, propylene glycol phenyl ether, propylene glycol diacetate, dipropylene glycol butyl ether, tripropylene glycol butyl ether, propylene glycol methyl ether, dipropylene glycol methyl ether, tripropylene glycol methyl ether, oxyethylenated (40 EO ) castor oil, benzyl alcohol, triethyl citrate, 1,3-butylene glycol, diethyl phthalates, dibutyl phthalates, diisopropyl phthalates, diethyl adipate, dibutyl adipate, diisopropyl adipate, diethyl tartrate, dibutyl tartrate, diethyl phosphate, dibutyl phosphate, di(2-ethylhexyl) phosphate, glyceryl diacetate and glyceryl triacetate.

19. The composition of claim 1, further comprising at least one cosmetic additive in a proportion of 0.01 and 2% by weight relative to the total weight of the composition.

20. The composition of claim 19, wherein said cosmetic additive is selected from the group consisting of water-soluble thickeners, ultraviolet screening agents, perfumes, colorants and pigments.

21. The composition of claim 9, wherein said polycondensate is of isophthalic acid, diethylene glycol, and a sulphoaryl dicarboxylic acid substituted on an aromatic ring thereof with an —$SO_3M$ group, in which M is a hydrogen atom or a metal ion selected from the group consisting of $Na^+$, $Li^+$ and $K^+$.

22. The composition of claim 21, wherein said polycondensate is further of 1,4-cyclohexanedimethanol.

23. The composition of claim 21, wherein said polycondensate is further of a member selected from the group consisting of ethylene glycol, triethylene glycol, tetraethylene glycol and terephthalate.

* * * * *